(12) United States Patent
DesNoyer et al.

(10) Patent No.: US 7,749,263 B2
(45) Date of Patent: *Jul. 6, 2010

(54) POLY(ESTER AMIDE) FILLER BLENDS FOR MODULATION OF COATING PROPERTIES

(75) Inventors: Jessica Renee DesNoyer, San Jose, CA (US); Stephen Dirk Pacetti, San Jose, CA (US); Syed Faiyaz Shmed Hossainy, Fremont, CA (US); Lothar Kleiner, Los Altos, CA (US); Yiwen Tang, San Jose, CA (US); Gina Zhang, Fremont, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 227 days.

This patent is subject to a terminal disclaimer.

(21) Appl. No.: 11/970,490

(22) Filed: Jan. 7, 2008

(65) Prior Publication Data

US 2008/0167712 A1    Jul. 10, 2008

Related U.S. Application Data

(62) Division of application No. 10/976,551, filed on Oct. 29, 2004, now Pat. No. 7,390,497.

(51) Int. Cl.
*A61F 2/06* (2006.01)
*A61K 31/00* (2006.01)
*A61L 31/10* (2006.01)
*A61L 29/08* (2006.01)

(52) U.S. Cl. .................. 623/1.15; 424/422; 424/423; 514/1; 514/2; 623/1.42; 623/1.43; 623/1.44; 623/1.46; 623/1.47; 623/1.48; 623/1.49; 623/900

(58) Field of Classification Search .................. 424/422, 424/423; 514/1, 2; 623/1.15, 1.42, 1.43, 623/1.44, 1.46, 1.47, 1.48, 1.49, 900
See application file for complete search history.

(56) References Cited

U.S. PATENT DOCUMENTS

| | | | |
|---|---|---|---|
| 2,072,303 A | 3/1937 | Herrmann et al. |
| 2,386,454 A | 10/1945 | Frosch et al. |
| 3,773,737 A | 11/1973 | Goodman et al. |
| 3,849,514 A | 11/1974 | Gray, Jr. et al. |
| 4,226,243 A | 10/1980 | Shalaby et al. |
| 4,304,767 A | 12/1981 | Heller et al. |
| 4,329,383 A | 5/1982 | Joh |
| 4,343,931 A | 8/1982 | Barrows |
| 4,529,792 A | 7/1985 | Barrows |
| 4,611,051 A | 9/1986 | Hayes et al. |
| 4,656,242 A | 4/1987 | Swan et al. |
| 4,733,665 A | 3/1988 | Palmaz |
| 4,800,882 A | 1/1989 | Gianturco |
| 4,882,168 A | 11/1989 | Casey et al. |
| 4,886,062 A | 12/1989 | Wiktor |
| 4,931,287 A | 6/1990 | Bae et al. |
| 4,941,870 A | 7/1990 | Okada et al. |
| 4,977,901 A | 12/1990 | Ofstead |
| 5,019,096 A | 5/1991 | Fox, Jr. et al. |
| 5,100,992 A | 3/1992 | Cohn et al. |
| 5,112,457 A | 5/1992 | Marchant |
| 5,133,742 A | 7/1992 | Pinchuk |
| 5,163,952 A | 11/1992 | Froix |
| 5,165,919 A | 11/1992 | Sasaki et al. |
| 5,219,980 A | 6/1993 | Swidler |
| 5,258,020 A | 11/1993 | Froix |
| 5,272,012 A | 12/1993 | Opolski |
| 5,292,516 A | 3/1994 | Viegas et al. |
| 5,298,260 A | 3/1994 | Viegas et al. |
| 5,300,295 A | 4/1994 | Viegas et al. |
| 5,306,501 A | 4/1994 | Viegas et al. |
| 5,306,786 A | 4/1994 | Moens et al. |
| 5,328,471 A | 7/1994 | Slepian |
| 5,330,768 A | 7/1994 | Park et al. |
| 5,380,299 A | 1/1995 | Fearnot et al. |
| 5,417,981 A | 5/1995 | Endo et al. |
| 5,447,724 A | 9/1995 | Helmus et al. |
| 5,455,040 A | 10/1995 | Marchant |
| 5,462,990 A | 10/1995 | Hubbell et al. |
| 5,464,650 A | 11/1995 | Berg et al. |
| 5,485,496 A | 1/1996 | Lee et al. |
| 5,516,881 A | 5/1996 | Lee et al. |
| 5,569,463 A | 10/1996 | Helmus et al. |
| 5,578,073 A | 11/1996 | Haimovich et al. |

(Continued)

FOREIGN PATENT DOCUMENTS

DE    42 24 401    1/1994

(Continued)

OTHER PUBLICATIONS

U.S. Appl. No. 10/816,0672, filed Mar. 31, 2004, Dugan et al.

(Continued)

*Primary Examiner*—Ana L Woodward
(74) *Attorney, Agent, or Firm*—Squire Sanders & Dempsey LLP

(57) ABSTRACT

Provided herein is a PEA polymer blend and coatings or implantable devices formed therefrom.

16 Claims, 2 Drawing Sheets

U.S. PATENT DOCUMENTS

| | | | |
|---|---|---|---|
| 5,581,387 A | 12/1996 | Cahill |
| 5,584,877 A | 12/1996 | Miyake et al. |
| 5,605,696 A | 2/1997 | Eury et al. |
| 5,607,467 A | 3/1997 | Froix |
| 5,609,629 A | 3/1997 | Fearnot et al. |
| 5,610,241 A | 3/1997 | Lee et al. |
| 5,616,338 A | 4/1997 | Fox, Jr. et al. |
| 5,624,411 A | 4/1997 | Tuch |
| 5,628,730 A | 5/1997 | Shapland et al. |
| 5,644,020 A | 7/1997 | Timmermann et al. |
| 5,649,977 A | 7/1997 | Campbell |
| 5,658,995 A | 8/1997 | Kohn et al. |
| 5,667,767 A | 9/1997 | Greff et al. |
| 5,670,558 A | 9/1997 | Onishi et al. |
| 5,674,242 A | 10/1997 | Phan et al. |
| 5,679,400 A | 10/1997 | Tuch |
| 5,700,286 A | 12/1997 | Tartaglia et al. |
| 5,702,754 A | 12/1997 | Zhong |
| 5,711,958 A | 1/1998 | Cohn et al. |
| 5,716,981 A | 2/1998 | Hunter et al. |
| 5,721,131 A | 2/1998 | Rudolph et al. |
| 5,723,219 A | 3/1998 | Kolluri et al. |
| 5,735,897 A | 4/1998 | Buirge |
| 5,746,998 A | 5/1998 | Torchilin et al. |
| 5,759,205 A | 6/1998 | Valentini |
| 5,776,184 A | 7/1998 | Tuch |
| 5,783,657 A | 7/1998 | Pavlin et al. |
| 5,788,979 A | 8/1998 | Alt et al. |
| 5,800,392 A | 9/1998 | Racchini |
| 5,820,917 A | 10/1998 | Tuch |
| 5,824,048 A | 10/1998 | Tuch |
| 5,824,049 A | 10/1998 | Ragheb et al. |
| 5,830,178 A | 11/1998 | Jones et al. |
| 5,837,008 A | 11/1998 | Berg et al. |
| 5,837,313 A | 11/1998 | Ding et al. |
| 5,849,859 A | 12/1998 | Acemoglu |
| 5,851,508 A | 12/1998 | Greff et al. |
| 5,854,376 A | 12/1998 | Higashi |
| 5,858,746 A | 1/1999 | Hubbell et al. |
| 5,861,387 A | 1/1999 | Labrie et al. |
| 5,865,814 A | 2/1999 | Tuch |
| 5,869,127 A | 2/1999 | Zhong |
| 5,873,904 A | 2/1999 | Ragheb et al. |
| 5,876,433 A | 3/1999 | Lunn |
| 5,877,224 A | 3/1999 | Brocchini et al. |
| 5,879,713 A | 3/1999 | Roth et al. |
| 5,902,875 A | 5/1999 | Roby et al. |
| 5,905,168 A | 5/1999 | Dos Santos et al. |
| 5,910,564 A | 6/1999 | Gruning et al. |
| 5,914,387 A | 6/1999 | Roby et al. |
| 5,919,893 A | 7/1999 | Roby et al. |
| 5,925,720 A | 7/1999 | Kataoka et al. |
| 5,932,299 A | 8/1999 | Katoot |
| 5,955,509 A | 9/1999 | Webber et al. |
| 5,958,385 A | 9/1999 | Tondeur et al. |
| 5,962,138 A | 10/1999 | Kolluri et al. |
| 5,971,954 A | 10/1999 | Conway et al. |
| 5,980,928 A | 11/1999 | Terry |
| 5,980,972 A | 11/1999 | Ding |
| 5,997,517 A | 12/1999 | Whitbourne |
| 6,010,530 A | 1/2000 | Goicoechea |
| 6,011,125 A | 1/2000 | Lohmeijer et al. |
| 6,015,541 A | 1/2000 | Greff et al. |
| 6,033,582 A | 3/2000 | Lee et al. |
| 6,034,204 A | 3/2000 | Mohr et al. |
| 6,042,875 A | 3/2000 | Ding et al. |
| 6,051,576 A | 4/2000 | Ashton et al. |
| 6,051,648 A | 4/2000 | Rhee et al. |
| 6,054,553 A | 4/2000 | Groth et al. |
| 6,056,993 A | 5/2000 | Leidner et al. |
| 6,060,451 A | 5/2000 | DiMaio et al. |
| 6,060,518 A | 5/2000 | Kabanov et al. |
| 6,080,488 A | 6/2000 | Hostettler et al. |
| 6,096,070 A | 8/2000 | Ragheb et al. |
| 6,099,562 A | 8/2000 | Ding et al. |
| 6,110,188 A | 8/2000 | Narciso, Jr. |
| 6,110,483 A | 8/2000 | Whitbourne et al. |
| 6,113,629 A | 9/2000 | Ken |
| 6,120,491 A | 9/2000 | Kohn et al. |
| 6,120,536 A | 9/2000 | Ding et al. |
| 6,120,788 A | 9/2000 | Barrows |
| 6,120,904 A | 9/2000 | Hostettler et al. |
| 6,121,027 A | 9/2000 | Clapper et al. |
| 6,129,761 A | 10/2000 | Hubbell |
| 6,136,333 A | 10/2000 | Cohn et al. |
| 6,143,354 A | 11/2000 | Koulik et al. |
| 6,153,252 A | 11/2000 | Hossainy et al. |
| 6,159,978 A | 12/2000 | Myers et al. |
| 6,165,212 A | 12/2000 | Dereume et al. |
| 6,172,167 B1 | 1/2001 | Stapert et al. |
| 6,177,523 B1 | 1/2001 | Reich et al. |
| 6,180,632 B1 | 1/2001 | Myers et al. |
| 6,203,551 B1 | 3/2001 | Wu |
| 6,211,249 B1 | 4/2001 | Cohn et al. |
| 6,214,901 B1 | 4/2001 | Chudzik et al. |
| 6,231,600 B1 | 5/2001 | Zhong |
| 6,240,616 B1 | 6/2001 | Yan |
| 6,245,753 B1 | 6/2001 | Byun et al. |
| 6,245,760 B1 | 6/2001 | He et al. |
| 6,248,129 B1 | 6/2001 | Froix |
| 6,251,136 B1 | 6/2001 | Guruwaiya et al. |
| 6,254,632 B1 | 7/2001 | Wu et al. |
| 6,258,121 B1 | 7/2001 | Yang et al. |
| 6,258,371 B1 | 7/2001 | Koulik et al. |
| 6,262,034 B1 | 7/2001 | Mathiowitz et al. |
| 6,270,788 B1 | 8/2001 | Koulik et al. |
| 6,277,449 B1 | 8/2001 | Kolluri et al. |
| 6,283,947 B1 | 9/2001 | Mirzaee |
| 6,283,949 B1 | 9/2001 | Roorda |
| 6,284,305 B1 | 9/2001 | Ding et al. |
| 6,287,628 B1 | 9/2001 | Hossainy et al. |
| 6,299,604 B1 | 10/2001 | Ragheb et al. |
| 6,306,176 B1 | 10/2001 | Whitbourne |
| 6,331,313 B1 | 12/2001 | Wong et al. |
| 6,335,029 B1 | 1/2002 | Kamath et al. |
| 6,344,035 B1 | 2/2002 | Chudzik et al. |
| 6,346,110 B2 | 2/2002 | Wu |
| 6,358,556 B1 | 3/2002 | Ding et al. |
| 6,365,172 B1 | 4/2002 | Barrows |
| 6,379,381 B1 | 4/2002 | Hossainy et al. |
| 6,387,379 B1 | 5/2002 | Goldberg et al. |
| 6,395,326 B1 | 5/2002 | Castro et al. |
| 6,419,692 B1 | 7/2002 | Yang et al. |
| 6,451,373 B1 | 9/2002 | Hossainy et al. |
| 6,482,834 B2 | 11/2002 | Spada et al. |
| 6,494,862 B1 | 12/2002 | Ray et al. |
| 6,503,538 B1 | 1/2003 | Chu et al. |
| 6,503,556 B2 | 1/2003 | Harish et al. |
| 6,503,954 B1 | 1/2003 | Bhat et al. |
| 6,506,437 B1 | 1/2003 | Harish et al. |
| 6,524,347 B1 | 2/2003 | Myers et al. |
| 6,527,801 B1 | 3/2003 | Dutta |
| 6,527,863 B1 | 3/2003 | Pacetti et al. |
| 6,528,526 B1 | 3/2003 | Myers et al. |
| 6,530,950 B1 | 3/2003 | Alvarado et al. |
| 6,530,951 B1 | 3/2003 | Bates et al. |
| 6,540,776 B2 | 4/2003 | Millare et al. |
| 6,544,223 B1 | 4/2003 | Kokish |
| 6,544,543 B1 | 4/2003 | Mandrusov et al. |
| 6,544,582 B1 | 4/2003 | Yoe |
| 6,555,157 B1 | 4/2003 | Hossainy |
| 6,558,733 B1 | 5/2003 | Hossainy et al. |
| 6,565,659 B1 | 5/2003 | Pacetti et al. |
| 6,572,644 B1 | 6/2003 | Moein |

| | | |
|---|---|---|
| 6,585,755 B2 | 7/2003 | Jackson et al. |
| 6,585,765 B1 | 7/2003 | Hossainy et al. |
| 6,585,926 B1 | 7/2003 | Mirzaee |
| 6,605,154 B1 | 8/2003 | Villareal |
| 6,616,765 B1 | 9/2003 | Hossainy et al. |
| 6,623,448 B2 | 9/2003 | Slater |
| 6,625,486 B2 | 9/2003 | Lundkvist et al. |
| 6,645,135 B1 | 11/2003 | Bhat |
| 6,645,195 B1 | 11/2003 | Bhat et al. |
| 6,656,216 B1 | 12/2003 | Hossainy et al. |
| 6,656,506 B1 | 12/2003 | Wu et al. |
| 6,660,034 B1 | 12/2003 | Mandrusov et al. |
| 6,663,662 B2 | 12/2003 | Pacetti et al. |
| 6,663,880 B1 | 12/2003 | Roorda et al. |
| 6,666,880 B1 | 12/2003 | Chiu et al. |
| 6,673,154 B1 | 1/2004 | Pacetti et al. |
| 6,673,385 B1 | 1/2004 | Ding et al. |
| 6,689,099 B2 | 2/2004 | Mirzaee |
| 6,695,920 B1 | 2/2004 | Pacetti et al. |
| 6,706,013 B1 | 3/2004 | Bhat et al. |
| 6,709,514 B1 | 3/2004 | Hossainy |
| 6,712,845 B2 | 3/2004 | Hossainy |
| 6,713,119 B2 | 3/2004 | Hossainy et al. |
| 6,716,444 B1 | 4/2004 | Castro et al. |
| 6,723,120 B2 | 4/2004 | Yan |
| 6,733,768 B2 | 5/2004 | Hossainy et al. |
| 6,740,040 B1 | 5/2004 | Mandrusov et al. |
| 6,743,462 B1 | 6/2004 | Pacetti |
| 6,749,626 B1 | 6/2004 | Bhat et al. |
| 6,753,071 B1 | 6/2004 | Pacetti et al. |
| 6,758,859 B1 | 7/2004 | Dang et al. |
| 6,759,054 B2 | 7/2004 | Chen et al. |
| 6,764,505 B1 | 7/2004 | Hossainy et al. |
| 6,926,919 B1 | 8/2005 | Hossainy et al. |
| 7,056,591 B1 | 6/2006 | Pacetti et al. |
| 7,063,884 B2 | 6/2006 | Hossainy et al. |
| 7,220,816 B2 | 5/2007 | Pacetti et al. |
| 2001/0007083 A1 | 7/2001 | Roorda |
| 2001/0014717 A1 | 8/2001 | Hossainy et al. |
| 2001/0018469 A1 | 8/2001 | Chen et al. |
| 2001/0020011 A1 | 9/2001 | Mathiowitz et al. |
| 2001/0029351 A1 | 10/2001 | Falotico et al. |
| 2001/0037145 A1 | 11/2001 | Guruwaiya et al. |
| 2001/0051608 A1 | 12/2001 | Mathiowitz et al. |
| 2002/0005206 A1 | 1/2002 | Falotico et al. |
| 2002/0007213 A1 | 1/2002 | Falotico et al. |
| 2002/0007214 A1 | 1/2002 | Falotico |
| 2002/0007215 A1 | 1/2002 | Falotico et al. |
| 2002/0009604 A1 | 1/2002 | Zamora et al. |
| 2002/0016625 A1 | 2/2002 | Falotico et al. |
| 2002/0032414 A1 | 3/2002 | Ragheb et al. |
| 2002/0032434 A1 | 3/2002 | Chudzik et al. |
| 2002/0051730 A1 | 5/2002 | Bodnar et al. |
| 2002/0071822 A1 | 6/2002 | Uhrich |
| 2002/0077693 A1 | 6/2002 | Barclay et al. |
| 2002/0082679 A1 | 6/2002 | Sirhan et al. |
| 2002/0087123 A1 | 7/2002 | Hossainy et al. |
| 2002/0091433 A1 | 7/2002 | Ding et al. |
| 2002/0094440 A1 | 7/2002 | Llanos et al. |
| 2002/0111590 A1 | 8/2002 | Davila et al. |
| 2002/0120326 A1 | 8/2002 | Michal |
| 2002/0123801 A1 | 9/2002 | Pacetti et al. |
| 2002/0142039 A1 | 10/2002 | Claude |
| 2002/0155212 A1 | 10/2002 | Hossainy |
| 2002/0165608 A1 | 11/2002 | Llanos et al. |
| 2002/0176849 A1 | 11/2002 | Slepian |
| 2002/0183581 A1 | 12/2002 | Yoe et al. |
| 2002/0188037 A1 | 12/2002 | Chudzik et al. |
| 2002/0188277 A1 | 12/2002 | Roorda et al. |
| 2003/0004141 A1 | 1/2003 | Brown |
| 2003/0028243 A1 | 2/2003 | Bates et al. |
| 2003/0028244 A1 | 2/2003 | Bates et al. |
| 2003/0031780 A1 | 2/2003 | Chudzik et al. |
| 2003/0032767 A1 | 2/2003 | Tada et al. |
| 2003/0036794 A1 | 2/2003 | Ragheb et al. |
| 2003/0039689 A1 | 2/2003 | Chen et al. |
| 2003/0040712 A1 | 2/2003 | Ray et al. |
| 2003/0040790 A1 | 2/2003 | Furst |
| 2003/0059520 A1 | 3/2003 | Chen et al. |
| 2003/0060877 A1 | 3/2003 | Falotico et al. |
| 2003/0065377 A1 | 4/2003 | Davila et al. |
| 2003/0072868 A1 | 4/2003 | Harish et al. |
| 2003/0073961 A1 | 4/2003 | Happ |
| 2003/0083646 A1 | 5/2003 | Sirhan et al. |
| 2003/0083739 A1 | 5/2003 | Cafferata |
| 2003/0097088 A1 | 5/2003 | Pacetti |
| 2003/0097173 A1 | 5/2003 | Dutta |
| 2003/0099712 A1 | 5/2003 | Jayaraman |
| 2003/0105518 A1 | 6/2003 | Dutta |
| 2003/0113439 A1 | 6/2003 | Pacetti et al. |
| 2003/0150380 A1 | 8/2003 | Yoe |
| 2003/0157241 A1 | 8/2003 | Hossainy et al. |
| 2003/0158517 A1 | 8/2003 | Kokish |
| 2003/0190406 A1 | 10/2003 | Hossainy et al. |
| 2003/0207020 A1 | 11/2003 | Villareal |
| 2003/0211230 A1 | 11/2003 | Pacetti et al. |
| 2004/0018296 A1 | 1/2004 | Castro et al. |
| 2004/0029952 A1 | 2/2004 | Chen et al. |
| 2004/0047978 A1 | 3/2004 | Hossainy et al. |
| 2004/0047980 A1 | 3/2004 | Pacetti et al. |
| 2004/0052858 A1 | 3/2004 | Wu et al. |
| 2004/0052859 A1 | 3/2004 | Wu et al. |
| 2004/0054104 A1 | 3/2004 | Pacetti |
| 2004/0060508 A1 | 4/2004 | Pacetti et al. |
| 2004/0062853 A1 | 4/2004 | Pacetti et al. |
| 2004/0063805 A1 | 4/2004 | Pacetti et al. |
| 2004/0071861 A1 | 4/2004 | Mandrusov et al. |
| 2004/0072922 A1 | 4/2004 | Hossainy et al. |
| 2004/0073298 A1 | 4/2004 | Hossainy |
| 2004/0086542 A1 | 5/2004 | Hossainy et al. |
| 2004/0086550 A1 | 5/2004 | Roorda et al. |
| 2004/0096504 A1 | 5/2004 | Michal |
| 2004/0098117 A1 | 5/2004 | Hossainy et al. |
| 2004/0170685 A1 * | 9/2004 | Carpenter et al. ............ 424/468 |
| 2005/0106204 A1 | 5/2005 | Hossainy et al. |
| 2005/0112171 A1 | 5/2005 | Tang et al. |
| 2005/0137381 A1 | 6/2005 | Pacetti et al. |
| 2005/0208091 A1 | 9/2005 | Pacetti |
| 2005/0245637 A1 | 11/2005 | Tang et al. |
| 2005/0265960 A1 | 12/2005 | Pacetti et al. |
| 2005/0271700 A1 | 12/2005 | Desnoyer et al. |
| 2006/0093842 A1 | 5/2006 | Desnoyer et al. |

FOREIGN PATENT DOCUMENTS

| | | |
|---|---|---|
| EP | 0 514 406 | 11/1992 |
| EP | 0 604 022 | 6/1994 |
| EP | 0 623 354 | 11/1994 |
| EP | 0 665 023 | 8/1995 |
| EP | 0 701 802 | 3/1996 |
| EP | 0 716 836 | 6/1996 |
| EP | 0 809 999 | 12/1997 |
| EP | 0 832 655 | 4/1998 |
| EP | 0 850 651 | 7/1998 |
| EP | 0 879 595 | 11/1998 |
| EP | 0 910 584 | 4/1999 |
| EP | 0 923 953 | 6/1999 |
| EP | 0 953 320 | 11/1999 |
| EP | 0 970 711 | 1/2000 |
| EP | 0 982 041 | 3/2000 |
| EP | 1 023 879 | 8/2000 |
| EP | 1 192 957 | 4/2002 |
| EP | 1 273 314 | 1/2003 |
| JP | 2001-190687 | 7/2001 |
| SU | 872531 | 10/1981 |
| SU | 876663 | 10/1981 |

| | | |
|---|---|---|
| SU | 905228 | 2/1982 |
| SU | 790725 | 2/1983 |
| SU | 1016314 | 5/1983 |
| SU | 811750 | 9/1983 |
| SU | 1293518 | 2/1987 |
| SU | 0 301 856 | 2/1989 |
| SU | 0 396 429 | 11/1990 |
| WO | WO 91/12846 | 9/1991 |
| WO | WO 94/09760 | 5/1994 |
| WO | WO 95/10989 | 4/1995 |
| WO | WO 95/24929 | 9/1995 |
| WO | WO 96/40174 | 12/1996 |
| WO | WO 97/10011 | 3/1997 |
| WO | WO 97/45105 | 12/1997 |
| WO | WO 97/46590 | 12/1997 |
| WO | WO 98/08463 | 3/1998 |
| WO | WO 98/17331 | 4/1998 |
| WO | WO 98/32398 | 7/1998 |
| WO | WO 98/36784 | 8/1998 |
| WO | WO 99/01118 | 1/1999 |
| WO | WO 99/38546 | 8/1999 |
| WO | WO 99/63981 | 12/1999 |
| WO | WO 00/02599 | 1/2000 |
| WO | WO 00/12147 | 3/2000 |
| WO | WO 00/18446 | 4/2000 |
| WO | WO 00/64506 | 11/2000 |
| WO | WO 01/01890 | 1/2001 |
| WO | WO 01/15751 | 3/2001 |
| WO | WO 01/17577 | 3/2001 |
| WO | WO 01/45763 | 6/2001 |
| WO | WO 01/49338 | 7/2001 |
| WO | WO 01/51027 | 7/2001 |
| WO | WO 01/74414 | 10/2001 |
| WO | WO 02/03890 | 1/2002 |
| WO | WO 02/18477 | 3/2002 |
| WO | WO 02/26162 | 4/2002 |
| WO | WO 02/34311 | 5/2002 |
| WO | WO 02/056790 | 7/2002 |
| WO | WO 02/058753 | 8/2002 |
| WO | WO 02/102283 | 12/2002 |
| WO | WO 03/000308 | 1/2003 |
| WO | WO 03/022323 | 3/2003 |
| WO | WO 03/028780 | 4/2003 |
| WO | WO 03/037223 | 5/2003 |
| WO | WO 03/039612 | 5/2003 |
| WO | WO 03/080147 | 10/2003 |
| WO | WO 03/082368 | 10/2003 |
| WO | WO 2004/000383 | 12/2003 |
| WO | WO 2004/009145 | 1/2004 |
| WO | WO 2005/061024 | 7/2005 |
| WO | WO 2005/089824 | 9/2005 |
| WO | WO 2005/097220 | 10/2005 |
| WO | WO 2005/118681 | 12/2005 |
| WO | WO 2006/004792 | 1/2006 |

OTHER PUBLICATIONS

Anonymous, *Cardiologists Draw—Up the Dream Stent*, Clinica 710:15 (Jun. 17, 1996), http://www.dialogweb.com/cgi/document?req=1061848202959, printed Aug. 25, 2003 (2 pages).

Anonymous, *Heparin-coated stents cut complications by 30%*, Clinica 732:17 (Nov. 18, 1996), http://www.dialogweb.com/cgi/document?req=1061847871753, printed Aug. 25, 2003 (2 pages).

Anonymous, *Rolling Therapeutic Agent Loading Device for Therapeutic Agent Delivery or Coated Stent* (Abstract 434009), Res. Disclos. pp. 974-975 (Jun. 2000).

Anonymous, *Stenting continues to dominate cardiology*, Clinica 720:22 (Sep. 2, 1996), http://www.dialogweb.com/cgi/document?req=1061848017752, printed Aug. 25, 2003 (2 pages).

Aoyagi et al., *Preparation of cross-linked aliphatic polyester and application to thermo-responsive material*, Journal of Controlled Release 32:87-96 (1994).

Barath et al., *Low Dose of Antitumor Agents Prevents Smooth Muscle Cell Proliferation After Endothelial Injury*, JACC 13(2): 252A (Abstract) (Feb. 1989).

Barbucci et al., *Coating of commercially available materials with a new heparinizable material*, J. Biomed. Mater. Res. 25:1259-1274 (Oct. 1991).

Chandrasekar et al., *Coronary Artery Endothelial Protection After Local Delivery of 17β-Estradiol During Balloon Angioplasty in a Porcine Model: A Potential New Pharmacologic Approach to Improve Endothelial Function*, J. of Am. College of Cardiology, vol. 38, No. 5, (2001) pp. 1570-1576.

Chung et al., *Inner core segment design for drug delivery control of thermo-responsive polymeric micelles*, Journal of Controlled Release 65:93-103 (2000).

De Lezo et al., *Intracoronary Ultrasound Assessment of Directional Coronary Atherectomy: Immediate and Follow-Up Findings*, JACC vol. 21, No. 2, (1993) pp. 298-307.

Dev et al., *Kinetics of Drug Delivery to the Arterial Wall Via Polyurethane-Coated Removable Nitinol Stent: Comparative Study of Two Drugs*, Catheterization and Cardiovascular Diagnosis 34:272-278 (1995).

Dichek et al., *Seeding of Intravascular Stents with Genetically Engineered Endothelial Cells*, Circ. 80(5):1347-1353 (Nov. 1989).

Eigler et al., *Local Arterial Wall Drug Delivery from a Polymer Coated Removable Metallic Stent: Kinetics, Distribution, and Bioactivity of Forskolin*, JACC, 4A (701-1), Abstract (Feb. 1994).

Helmus, *Overview of Biomedical Materials*, MRS Bulletin, pp. 33-38 (Sep. 1991).

Herdeg et al., *Antiproliferative Stent Coatings: Taxol and Related Compounds*, Semin. Intervent. Cardiol. 3:197-199 (1998).

Huang et al., *Biodegradable Polymers Derived from Aminoacids*, Macromol. Symp. 144, 7-32 (1999).

Inoue et al., *An AB block copolymer of oligo(methyl methacrylate) and poly(acrylic acid) for micellar delivery of hydrophobic drugs*, Journal of Controlled Release 51:221-229 (1998).

International Search Report and Written Opinion for PCT/US2005/038029, filed Oct. 21, 2005, mailed Mar. 1, 2006, 11 pgs.

Kataoka et al., *Block copolymer micelles as vehicles for drug delivery*, Journal of Controlled Release 24:119-132 (1993).

Katsarava et al., *Amino Acid-Based Bioanalogous Polymers. Synthesis and Study of Regular Poly(ester amide)s Based on Bis(α-amino acid)α,ω-Alkylene Diesters, and Aliphatic Dicarbolic Acids*, Journal of Polymer Science, Part A: Polymer Chemistry, 37(4), 391-407 (1999).

Levy et al., *Strategies for Treating Arterial Restenosis Using Polymeric Controlled Release Implants*, Biotechnol. Bioact. Polym. [Proc. Am. Chem. Soc. Symp.], pp. 259-268 (1994).

Liu et al., "Intermolecular Complexation Between PEG/PBT Block Copolymer and Polyelectrolytes Poly-Acrylic Acid and Maleic Acid Copolymer", Eur. Polym, J., vol. 33, No. 7, pp. 1041-1047, 1997.

Liu et al., *Drug release characteristics of unimolecular polymeric micelles*, Journal of Controlled Release 68:167-174 (2000).

Marconi et al., *Covalent bonding of heparin to a vinyl copolymer for biomedical applications*, Biomaterials 18(12):885-890 (1997).

Matsumaru et al., *Embolic Materials for Endovascular Treatment of Cerebral Lesions*, J. Biomater. Sci. Polymer Edn 8(7):555-569 (1997).

Miyazaki et al., *Antitumor Effect of Implanted Ethylene-Vinyl Alcohol Copolymer Matrices Containing Anticancer Agents on Ehrlich Ascites Carcinoma and P388 Leukemia in Mice*, Chem. Pharm. Bull. 33(6) 2490-2498 (1985).

Miyazawa et al., *Effects of Pemirolast and Tranilast on Intimal Thickening After Arterial Injury in the Rat*, J. Cardiovasc. Pharmacol., pp. 157-162 (1997).

Moreno et al., *Macrophage Infiltration Predicts Restenosis After Coronary Intervention in Patients with Unstable Angina*, Circulation, vol. 94, No. 12, (1996) pp. 3098-3102.

Nordrehaug et al., *A novel biocompatible coating applied to coronary stents*, EPO Heart Journal 14, p. 321 (P1694), Abstr. Suppl. (1993).

Ohsawa et al., *Preventive Effects of an Antiallergic Drug, Pemirolast Potassium, on Restenosis After Percutaneous Transluminal Coronary Angioplasty*, American Heart Journal 136(6):1081-1087 (Dec. 1998).

Oikawa et al., *Mechanisms of Acute Gain and Late Lumen Loss After Atherectomy in Different Preintervention Arterial Remodeling Patterns*, The Am. J. of Cardilogy, vol. 89, (2002) pp. 505-510.

Ozaki et al., *New Stent Technologies*, Progress in Cardiovascular Diseases, vol. XXXIX(2):129-140 (Sep./Oct. 1996).

Pechar et al., *Poly(ethylene glycol) Multiblock Copolymer as a Carrier of Anti-Cancer Drug Doxorubicin*, Bioconjucate Chemistry 11(2):131-139 (Mar./Apr. 2000).

Peng et al., *Role of polymers in improving the results of stenting in coronary arteries*, Biomaterials 17:685-694 (1996).

Saotome, et al., *Novel Enzymatically Degradable Polymers Comprising α-Amino Acid, 1,2-Ethanediol, and Adipic Acid*, Chemistry Letters, pp. 21-24, (1991).

Scully et al., *Effect of a heparan sulphate with high affinity for antithrombin III upon inactivation of thrombin and coagulaton Factor Xa*, Biochem J. 262, (1989) pp. 651-658.

Shigeno, *Prevention of Cerebrovascular Spasm by Bosentan, Novel Endothelin Receptor*, Chemical Abstract 125:212307 (1996).

van Beusekom et al., *Coronary stent coatings*, Coronary Artery Disease 5(7):590-596 (Jul. 1994).

Virmani et al., *Lessons From Sudden Coronary Death a Comprehensive Morphological Classification Scheme for Atherosclerotic Lesions*, Arterioscler Thromb Vasc Biol. (2000) pp. 1262-1275.

Wilensky et al., *Methods and Devices for Local Drug Delivery in Coronary and Peripheral Arteries*, Trends Cardiovasc. Med. 3(5):163-170 (1993).

Yokoyama et al., *Characterization of physical entrapment and chemical conjugation of adriamycin in polymeric micelles and their design for in vivo delivery to a solid tumor*, Journal of Controlled Release 50:79-92 (1998).

* cited by examiner

POLY(ESTER AMIDE) FILLER BLENDS FOR MODULATION OF COATING PROPERTIES

CROSS-REFERENCE TO RELATED APPLICATION

This is a divisional application of U.S. application No. 10/976,551, filed on Oct. 29, 2004, issued as U.S. Pat. No. 7,390,497, the teaching of which is incorporated herein by reference in its entirety.

BACKGROUND OF THE INVENTION

1. Field of the Invention

This invention generally relates to poly(ester amide) (PEA) polymer blends having a PEA polymer and a material or polymer capable of hydrogen-bonding with the PEA polymer, which have a glass transition temperature ($T_g$) higher than the PEA polymer and are useful for coating an implantable device such as a drug-delivery stent.

2. Description of the Background

Poly(ester amide) polymers are known for their relatively low glass transition temperatures. For example, co-poly-{[N,N'-sebacoyl-bis-(L-leucine)-1,6-hexylene diester]-[N,N'-sebacoyl-L-lysine benzyl ester]} (PEA-Bz) and co-poly{[N,N'-sebacoyl-bis-(L-leucine)-1,6-hexylene diester]-[N,N'-sebacoyl-L-lysine 4-amino-TEMPO amide]} (PEA-TEMPO) have a $T_g$ of approximately 23° C. and 33° C., respectively.

Complications related to low $T_g$ manifest themselves as reduced release rate control, potential sticking and adhesion to the delivery balloon, and reduced shelf life stability. Low $T_g$ materials have higher drug permeabilities, which necessitates the use of greater amounts of polymer to control release rate of the drug. Moreover, the low $T_g$ can enable the drug to diffuse within the coating. In other words, the drug configuration within a given coating can change with time until an equilibrium state is reached, resulting in release rate shifts. Low $T_g$ materials also tend to be softer, they can be more adhesive to balloons, and are more prone to failure during mechanical perturbations such as crimping and expansion.

The embodiments of the present invention provide for methods addressing these issues.

SUMMARY OF THE INVENTION

Provided herein are poly(ester amide) (PEA) compositions that include one or more PEA polymers and a material capable of hydrogen bonding with the PEA molecules. The PEA compositions provided herein can form coatings that have improved stability, drug release rate, and mechanical characteristics. The PEA compositions can also be used to form the implantable device itself, one example of which is a stent.

In some embodiments, the PEA polymer blends can be used optionally with a biobeneficial material and/or optionally a bioactive agent to coat an implantable device. In some other embodiments, the PEA polymer blends can be used with one or more biocompatible polymers, which can be biodegradable, bioabsorbable, non-degradable, or non-bioabsorbable polymer.

The implantable device can be a stent that can be a metallic, biodegradable or nondegradable stent. The stent can be intended for neurovasculature, carotid, coronary, pulmonary, aorta, renal, biliary, iliac, femoral, popliteal, or other peripheral vasculature. The stent can be used to treat or prevent a disorder such as atherosclerosis, thrombosis, restenosis, hemorrhage, vascular dissection or perforation, vascular aneurysm, vulnerable plaque, chronic total occlusion, claudication, anastomotic proliferation for vein and artificial grafts, bile duct obstruction, ureter obstruction, tumor obstruction, or combinations thereof.

BRIEF DESCRIPTION OF THE DRAWINGS

FIG. 1a shows the SEM of the stents with coatings of configuration 1; FIG. 1b shows the SEM of the stents with coatings of configuration 2, and FIG. 1c shows the SEM of the stents with coatings of configuration 3. Configurations 1-3 are described in Example 1.

DETAILED DESCRIPTION

Figure 1A:
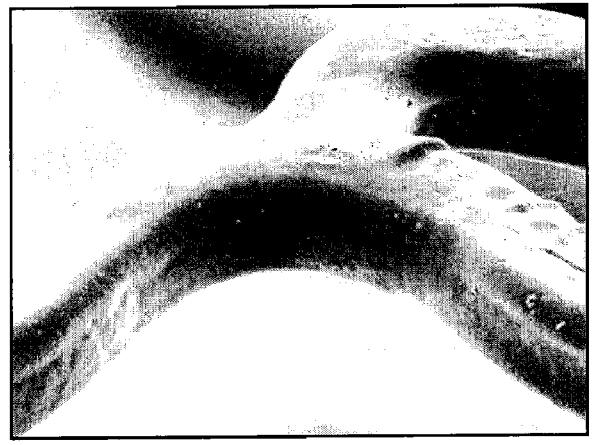
FIGS. 1a, 1b and 1c are SEM (scanning electron micrographs) of stents coated with poly(ester amide) and PolyActive™.

Provided herein are poly(ester amide) (PEA) compositions that include one or more PEA polymers and a material capable of hydrogen bonding with the PEA molecules. The PEA compositions provided herein can form coatings that have improved stability, drug release rate, and mechanical characteristics. The PEA compositions can also be used to form the implantable device itself, one example of which is a stent.

In some embodiments, the PEA polymer blends can be used optionally with a biobeneficial material and/or optionally a bioactive agent to coat an implantable device. In some other embodiments, the PEA polymer blends can be used with one or more biocompatible polymers, which can be biodegradable, bioabsorbable, non-degradable, or non-bioabsorbable polymer.

The implantable device can be a stent that can be a metallic, biodegradable or nondegradable stent. The stent can be intended for neurovasculature, carotid, coronary, pulmonary, aorta, renal, biliary, iliac, femoral, popliteal, or other peripheral vasculature. The stent can be used to treat or prevent a disorder such as atherosclerosis, thrombosis, restenosis, hemorrhage, vascular dissection or perforation, vascular aneurysm, vulnerable plaque, chronic total occlusion, claudication, anastomotic proliferation for vein and artificial grafts, bile duct obstruction, ureter obstruction, tumor obstruction, or combinations thereof.

Polymers Capable of Forming Hydrogen Bonds with poly(ester amide)

Hydrogen bonding is an important form of molecule-molecule interactions that occur between hydrogen atoms bonded to an atom with high electronic negativity, typically fluorine, oxygen and nitrogen, and the unshared electron pairs located on other electronegative atoms. A hydrogen bond can be generally described as $X_1$—H—$X_2$, where $X_2$ can be an electronic donor or acceptor and $X_1$ and $X_2$ are independently fluorine, oxygen, or nitrogen atoms or groupings.

The amide groups in the PEA polymer backbone can participate in hydrogen bonding as both donors and acceptors. This behavior is well known in nylon polymers. However, the stereochemistry of the PEA chain is such that a close packed arrangement, which would allow for hydrogen bonding between the polymer chains, does not occur. In order to elicit an interaction between PEA chains, polymeric fillers can be added to PEA. These fillers can serve as a bridge between PEA chains if they are capable of hydrogen bonding. In this way, the amide groups in the PEA chain can hydrogen bond to the filler, which, in turn, can hydrogen bond to another PEA chain, thereby reducing the mobility of the PEA polymer chains and thus increasing the effective $T_g$ of the material.

As used herein, poly(ester amide) encompasses a polymer having at least one ester grouping and at least one amide grouping in the backbone. One example is the PEA polymer made according to Scheme I. Other PEA polymers are described in U.S. Pat. No. 6,503,538 B1. An example of the PEA polymer includes diacid, diol, and amino acid subunits, the pendant groups of which may or may not include biobeneficial moieties.

perature graph for a polymer. When an amorphous or semicrystalline polymer is heated, its coefficient of expansion and heat capacity both increase as the temperature rises, indicating increased molecular motion. As the temperature rises, the sample's actual molecular volume remains constant. Therefore, a higher coefficient of expansion points to a free volume increase of the system and increased freedom of movement for the molecules. The increasing heat capacity corresponds to increasing heat dissipation through movement.

Scheme I

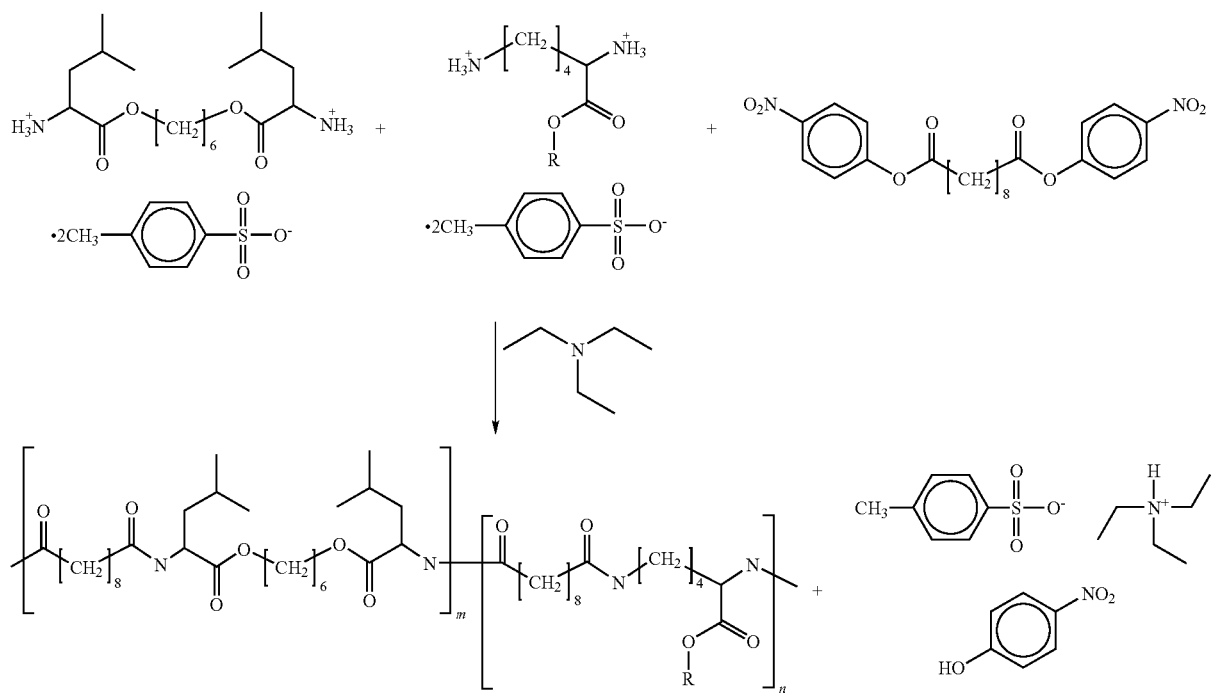

PEA polymers can be made by condensation polymerization utilizing, among others, diacids, diols, diamines, and amino acids. Some exemplary methods of making PEA are described in U.S. Pat. No. 6,503,538 B1.

Many polymers are capable of forming hydrogen bonds with the PEA polymer chain. To select a proper polymer filler, two conditions must be given: (1) it must be acceptable for the polymeric filler to be released, and (2) some hydrogen bonding polymers are hydrophilic and a very hydrophilic polymer will increase water absorption of the material, which lowers the $T_g$ of the material, increases drug diffusivity, and lowers the strength, negating the desired effect of increasing $T_g$ of the PEA material. Therefore, a preferred polymer filler will be capable of forming hydrogen bonds with the PEA polymer chain but will not substantially increase water absorption of the material. For example, such a polymer filler will have a hydrophicility close to or below about the hydrophicility of poly(vinyl alcohol).

$T_g$ as used herein generally refers to the temperature at which the amorphous domains of a polymer change from a brittle vitreous state to a plastic state at atmospheric pressure. In other words, $T_g$ corresponds to the temperature where the onset of segmental motion in the chains of the polymer occurs, and it is discernible in a heat-capacity-versus-tem- As used herein, the term "low $T_g$" refers to a $T_g$ of below about the $T_g$ of PEA-BZ ($T_g$=23° C.) or below about the $T_g$ of PEA-TEMPO ($T_g$=33° C.).

Suitable hydrogen bonding polymers can be biodegradable or non-degradable or durable polymers, or combinations thereof. Non-degradable polymers that may be blended with a PEA polymer must have a number-average molecular weight or weight-average molecular weight below approximately 40,000 Daltons to allow them to be secreted by the kidneys. Biodegradable polymers that may be blended with a PEA polymer must be able to degrade into fragments having a number-average or weight-average molecular weight below about 40,000 Daltons to allow them to be secreted by the kidneys. Specific non-degradable polymer candidates include, but are not limited to, polymers or copolymers of monomers containing a hydroxyl group, a carboxyl group or an amino group, examples of which are poly(vinyl alcohol), poly(vinyl alcohol-co-vinyl acetate), polyacrylic acid, poly (ethylene-co-acrylic acid), polymethacrylic acid, poly(ethylene-co-vinyl alcohol), poly(acrylamide), poly(hydroxypropyl methacrylamide), poly(2-hydroxyethyl methacrylate), poly(2-methoxyethyl methacrylate), poly(2-ethoxyethyl methacrylate), poly(2-methoxyethyl acrylate), poly(vinyl pyrrolidone), poly(pyrrole), (non-water soluble cellulose acetate, non-water soluble hydroxyethyl cellulose, non-water soluble hydroxypropyl cellulose, cellulose ethers such as methyl cellulose and ethyl cellulose, , poly(urethanes), poly (urethane-ureas), poly(ureas), poly(tetramethylene glycol), poly(propylene glycol), poly(ethylene glycol), and combinations thereof.

In some embodiments, biodegradable polymers capable of hydrogen bonding with PEA polymers can be, for example, poly(imino carbonates), peptides, gelatin, collagen, non-water soluble chitosan, agarose, elastin, poly(alginic acid), alginate, dextrose, dextran, poly(glutamic acid), poly(lysine), copolymers containing poly(ethylene glycol) and polybutylene terephthalate segments (PEG/PBT) (PolyActive™), poly(aspartic acid), poly(leucine), poly(leucine-co-hydroxyethyl glutamine), poly(benzyl glutamate), poly(glutamic acid-co-ethyl glutamate), poly(amino acids), or a combination thereof. poly(ortho esters), poly(anhydrides), poly(D,L-lactic acid), poly (L-lactic acid), poly(glycolic acid), copolymers of poly(lactic) and glycolic acid, poly(phospho esters), poly(β-hydroxybutyrate), poly(caprolactone), poly(trimethylene carbonate), poly(oxaesters), poly(oxaamides), poly (ethylene carbonate), poly(propylene carbonate), poly(phosphoesters), poly(phosphazenes), copolymers thereof with PEG, or combinations thereof.

In some embodiments, the hydrogen-bonding filler can be a block copolymer having flexible poly(ethylene glycol) and poly(butylene terephthalate) blocks (PEGT/PBT) (e.g., PolyActive™). PolyActive™ is intended to include AB, ABA, BAB copolymers having such segments of PEG and PBT (e.g., poly(ethylene glycol)-block-poly(butyleneterephthalate)-block poly(ethylene glycol)(PEG-PBT-PEG). PolyActive™ (commonly expressed in the formula XPEGTMPBTN where X is the molecular weight of the PEG segment, M is weight percentage of PEG segments, and N is the weight percentage of PBT segments) has PEG blocks or segments that can form hydrogen-bonding with PEA molecules in that the oxygen atom in PolyActive™ can act as a donor atom to form a hydrogen bond as shown below:

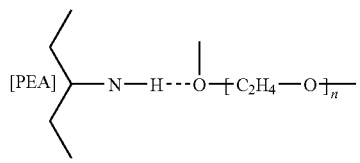

The carbonyl oxygens in the ester linkages of PolyActive™ can also act as hydrogen bond donor atoms. As a result, the $T_g$ of the PEA/PolyActive™ blend will be higher than that of PEA. In addition, the PEA component in the blend will have drug-release properties better than PolyActive™ alone because PolyActive™ does not give good drug-release control when used alone. In this embodiment, the PEA and PolyActive™ can be used as a blend to coat an implantable device or to form the implantable device itself or in separate layers to coat an implantable device. For example, the PEA/PolyActive™ blend can be coated onto a stent as a drug delivery matrix. Alternatively, the PEA and PolyActive™ can be coated onto an implantable device in separate layers, where, in the interphase between a PolyActive™ and a PEA layer, the hydrogen-bonding shown above may still exist between the PolyActive molecules and the PEA molecules at the interface. In one embodiment, the PEA can be conjugated to a biobeneficial moiety. The biobeneficial moiety is derived from a biobeneficial material defined below. For example, the PEA/biobeneficial moiety conjugate can be PEA-PEG, PEA-phosphoryl choline (PEA-PC), or PEA-choline.

In some other embodiments, dendrimers and/or star-shaped polymers having —$NH_2$ or —COOH pendant or end groups can be blended into PEA to facilitate hydrogen-bonding. The star polymers or dendrimers can contain a conjugated active agent in addition to the hydrogen bonding moieties such as —COOH or —$NH_2$. Other filler materials such as an absorbable glass with Fe, Ca and/or P can be blended into a PEA polymer. The electrostatic interaction may also enhance the $T_g$ of the blend thus formed.

In some embodiments, the hydrogen-bonding filler polymers can be a bioactive component that would modulate biological outcome additively or synergistically with a drug in a drug-delivery coating formed of a PEA polymer. Such bioactive component can be, for example, laminin V, silk elastin, or hyaluronic acid-benzyl ester for faster healing, resten NG, or other antisense oligonucleotide fragment with antiproliferative properties, MMPI for preventing SMC migration, and/or cellulose acetate-co-pentasaccharide for local factor Xa inhibition, etc.

Biobeneficial Material

The PEA with hydrogen-bonding fillers can form a coating optionally with a biobeneficial material. The combination can be mixed, blended, or coated in separate layers. The biobeneficial material useful in the coatings described herein can be a polymeric material or non-polymeric material. The biobeneficial material is preferably non-toxic, non-antigenic and non-immunogenic. A biobeneficial material is one that enhances the biocompatibility of a device by being non-fouling, hemocompatible, actively non-thrombogenic, or anti-inflammatory, all without depending on the release of a pharmaceutically active agent.

Representative biobeneficial materials include, but are not limited to, polyethers such as poly(ethylene glycol), copoly(ether-esters) (e.g. PEO/PLA); polyalkylene oxides such as poly(ethylene oxide), poly(propylene oxide), poly(ether ester), polyalkylene oxalates, polyphosphazenes, phosphoryl choline, choline, poly(aspirin), polymers and co-polymers of hydroxyl bearing monomers such as hydroxyethyl methacrylate (HEMA), hydroxypropyl methacrylate (HPMA), hydroxypropylmethacrylamide, poly (ethylene glycol) acrylate (PEGA), PEG methacrylate, 2-methacryloyloxyethylphosphorylcholine (MPC) and n-vinyl pyrrolidone (VP), carboxylic acid bearing monomers such as methacrylic acid (MA), acrylic acid (AA), alkoxymethacrylate, alkoxyacrylate, and 3-trimethylsilylpropyl methacrylate (TMSPMA), poly(styrene-isoprene-styrene)-PEG (SIS-PEG), polystyrene-PEG, polyisobutylene-PEG, polycaprolactone-PEG (PCL-PEG), PLA-PEG, poly(methyl methacrylate)-PEG (PMMA-PEG), polydimethylsiloxane-co-PEG (PDMS-PEG), poly(vinylidene fluoride)-PEG (PVDF-PEG), PLURONIC™ surfactants (polypropylene oxide-co-polyethylene glycol), poly(tetramethylene glycol), hydroxy functional poly(vinyl pyrrolidone), biomolecules such as fibrin, fibrinogen, cellulose, starch, collagen, dextran, dextrin, hyaluronic acid, fragments and derivatives of hyaluronic acid, heparin, fragments and derivatives of heparin, glycosamino glycan (GAG), GAG derivatives, polysaccharide, elastin, chitosan, alginate, silicones, and combinations thereof. In some embodiments, the coating can exclude any one of the aforementioned polymers.

In a further embodiment, the biobeneficial material can be garlic oil, fullerene, metallic materials such as Ca, Mg, and Tantalum ions.

In a preferred embodiment, the biobeneficial material can include a polyether such as poly(ethylene glycol) (PEG) or polyalkylene oxide.

Bioactive Agents

The polymeric coatings or the polymeric substrate described herein may optionally include one or more bioactive agents. These bioactive agents can be any agent which is a therapeutic, prophylactic, or diagnostic agent. These agents can have anti-proliferative or anti-inflammatory properties or can have other properties such as antineoplastic, antiplatelet, anti-coagulant, anti-fibrin, antithrombonic, antimitotic, antibiotic, antiallergic, antioxidant as well as cystostatic agents. Examples of suitable therapeutic and prophylactic agents include synthetic inorganic and organic compounds, proteins and peptides, polysaccharides and other sugars, lipids, and DNA and RNA nucleic acid sequences having therapeutic, prophylactic or diagnostic activities. Nucleic acid sequences include genes, antisense molecules that bind to complementary DNA to inhibit transcription, and ribozymes. Some other examples of other bioactive agents include antibodies, receptor ligands, enzymes, adhesion peptides, blood clotting factors, inhibitors or clot dissolving agents such as streptokinase and tissue plasminogen activator, antigens for immunization, hormones and growth factors, oligonucleotides such as antisense oligonucleotides and ribozymes and retroviral vectors for use in gene therapy. Examples of anti-proliferative agents include rapamycin and its functional or structural derivatives, 40-O-(2-hydroxy)ethyl-rapamycin (everolimus), and its functional or structural derivatives, paclitaxel and its functional and structural derivatives. Examples of rapamycin derivatives include methyl rapamycin (ABT-578), 40-O-(3-hydroxy)propyl-rapamycin, 40-O-[2-(2-hydroxy)ethoxy]ethyl-rapamycin, and 40-O-tetrazole-rapamycin. Examples of paclitaxel derivatives include docetaxel. Examples of antineoplastics and/or antimitotics include methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, thrombin inhibitors such as Angiomax ä (Biogen, Inc., Cambridge, Mass.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), nitric oxide or nitric oxide donors, super oxide dismutases, super oxide dismutase mimetic, 4-amino-2,2,6,6-tetramethylpiperidine-1-oxyl (4-amino-TEMPO), estradiol, anticancer agents, dietary supplements such as various vitamins, and a combination thereof. Examples of anti-inflammatory agents including steroidal and non-steroidal anti-inflammatory agents include tacrolimus, dexamethasone, clobetasol, combinations thereof. Examples of such cytostatic substance include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.). An example of an antiallergic agent is permirolast potassium. Other therapeutic substances or agents which may be appropriate include alpha-interferon, bioactive RGD, and genetically engineered epithelial cells. The foregoing substances can also be used in the form of prodrugs or co-drugs thereof. The foregoing substances are listed by way of example and are not meant to be limiting. Other active agents which are currently available or that may be developed in the future are equally applicable.

The dosage or concentration of the bioactive agent required to produce a favorable therapeutic effect should be less than the level at which the bioactive agent produces toxic effects and greater than the level at which non-therapeutic results are obtained. The dosage or concentration of the bioactive agent can depend upon factors such as the particular circumstances of the patient; the nature of the trauma; the nature of the therapy desired; the time over which the ingredient administered resides at the vascular site; and if other active agents are employed, the nature and type of the substance or combination of substances. Therapeutic effective dosages can be determined empirically, for example by infusing vessels from suitable animal model systems and using immunohistochemical, fluorescent or electron microscopy methods to detect the agent and its effects, or by conducting suitable in vitro studies. Standard pharmacological test procedures to determine dosages are understood by one of ordinary skill in the art.

Examples of Implantable Devices

As used herein, an implantable device may be any suitable medical substrate that can be implanted in a human or veterinary patient. Examples of such implantable devices include self-expandable stents, balloon-expandable stents, stent-grafts, grafts (e.g., aortic grafts), artificial heart valves, cerebrospinal fluid shunts, pacemaker electrodes, and endocardial leads (e.g., FINELINE and ENDOTAK, available from Guidant Corporation, Santa Clara, Calif.). The underlying structure of the device can be of virtually any design. The device can be made of a metallic material or an alloy such as, but not limited to, cobalt chromium alloy (ELGILOY), stainless steel (316L), high nitrogen stainless steel, e.g., BIODUR 108, cobalt chrome alloy L-605, "MP35N," "MP20N," ELASTINITE (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from Standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. Devices made from bioabsorbable or biostable polymers could also be used with the embodiments of the present invention. The device itself, such as a stent, can also be made from the described inventive polymers or polymer blends.

Method of Use

In accordance with embodiments of the invention, a coating of the various described embodiments can be formed on an implantable device or prosthesis, e.g., a stent. For coatings including one or more active agents, the agent will remain on the medical device such as a stent during delivery and expansion of the device, and released at a desired rate and for a predetermined duration of time at the site of implantation. Preferably, the medical device is a stent. A stent having the above-described coating is useful for a variety of medical procedures, including, by way of example, treatment of obstructions caused by tumors in bile ducts, esophagus, trachea/bronchi and other biological passageways. A stent having the above-described coating is particularly useful for treating occluded regions of blood vessels caused by abnormal or inappropriate migration and proliferation of smooth muscle cells, thrombosis, and restenosis. Stents may be placed in a wide array of blood vessels, both arteries and veins. Representative examples of sites include the iliac, renal, and coronary arteries.

For implantation of a stent, an angiogram is first performed to determine the appropriate positioning for stent therapy. An angiogram is typically accomplished by injecting a radiopaque contrasting agent through a catheter inserted into an artery or vein as an x-ray is taken. A guidewire is then advanced through the lesion or proposed site of treatment. Over the guidewire is passed a delivery catheter which allows a stent in its collapsed configuration to be inserted into the passageway. The delivery catheter is inserted either percutaneously or by surgery into the femoral artery, brachial artery, femoral vein, or brachial vein, and advanced into the appropriate blood vessel by steering the catheter through the vascular system under fluoroscopic guidance. A stent having the above-described coating may then be expanded at the desired area of treatment. A post-insertion angiogram may also be utilized to confirm appropriate positioning.

EXAMPLES

The embodiments of the present invention will be illustrated by the following set forth examples. All parameters and data are not to be construed to unduly limit the scope of the embodiments of the invention.

Example 1

Study of Stents Coated with the Combination of Poly(ester amide) and PolyActive™

Vision 12 mm small stents (available from Guidant Corporation) are coated according to the following configurations:

Configuration 1
Primer layer: 100 μg PolyActive™, from a 2% PolyActive™ (300PEGT55PBT45) solution in a solvent mixture of 1,1,2-trichloroethane and chloroform (80/20) (w/w), and baked at 50° C. for 1 hour;
Drug layer: 120 μg everolimus, coated from a 2% drug solution dissolved in a solvent mixture of acetone/xylene (60/40) (w/w), baked at 50° C. for 1 hour;
PEA release rate control layer: 100 μg PEA, coated from a 2% PEA solution in ethanol; baked at 50° C. for 1 hour;
PolyActive™ biobeneficial layer: 200 μg PolyActive™, coated from a 2% PolyActive™ (300PEGT55PBT45) solution in a solvent mixture of 1,1,2-trichloroethane and chloroform (80/20) (w/w), and baked at 50° C. for 1 hour.

Configuration 2
Primer layer: 100 μg PolyActive™, from a 2% PolyActive™ (300PEGT55PBT45) solution in a solvent mixture of 1,1,2-trichloroethane and chloroform (80/20) (w/w), and baked at 50° C. for 1 hour;
Drug layer: 120 μg everolimus, coated from a 2% drug solution dissolved in a solvent mixture of acetone/xylene (60/40) (w/w), and baked at 50° C. for 1 hour;
PEA release rate control layer: 200 μg PEA, coated from a 2% PEA solution in ethanol; baked at 50° C. for 1 hour;
PolyActive™ biobeneficial layer: 200 μg PolyActive™, coated from a 2% PolyActive™ (300PEGT55PBT45) solution in a solvent mixture of 1,1,2-trichloroethane and chloroform (80/20) (w/w), and baked at 50° C. for 1 hour.

Configuration 3
Primer layer: 100 μg PolyActive™, from a 2% PolyActive™ (300PEGT55PBT45) solution in a solvent mixture of 1,1,2-trichloroethane and chloroform (80/20) (w/w), and baked at 50° C. for 1 hour;
Drug layer: 120 μg everolimus, coated from a 2% drug solution dissolved in a solvent mixture of acetone/xylene (60/40) (w/w), and baked at 50° C. for 1 hour;
PEA release rate control layer: 400 μg PEA, coated from a 2% (w/w) PEA solution in ethanol; baked at 50° C. for 1 hour;
PolyActive™ biobeneficial layer: 200 μg PolyActive™, coated from a 2% PolyActive™ (300PEGT55PBT45) solution in a solvent mixture of 1,1,2-trichloroethane and chloroform (80/20) (w/w), and baked at 50° C. for 1 hour.

Figure 1B:
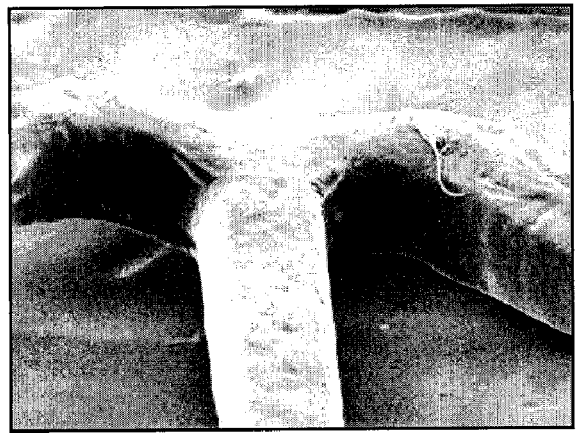
Figure 1C:
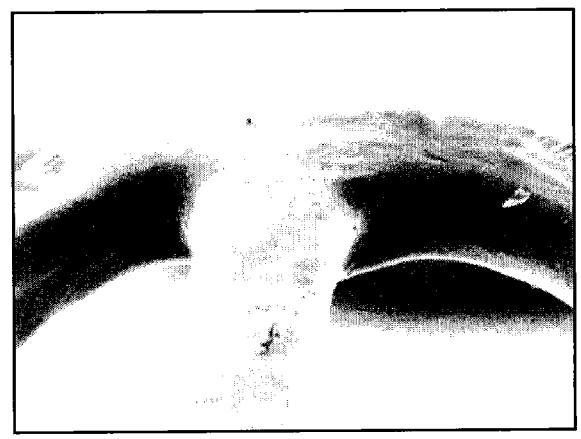
Figure 2:
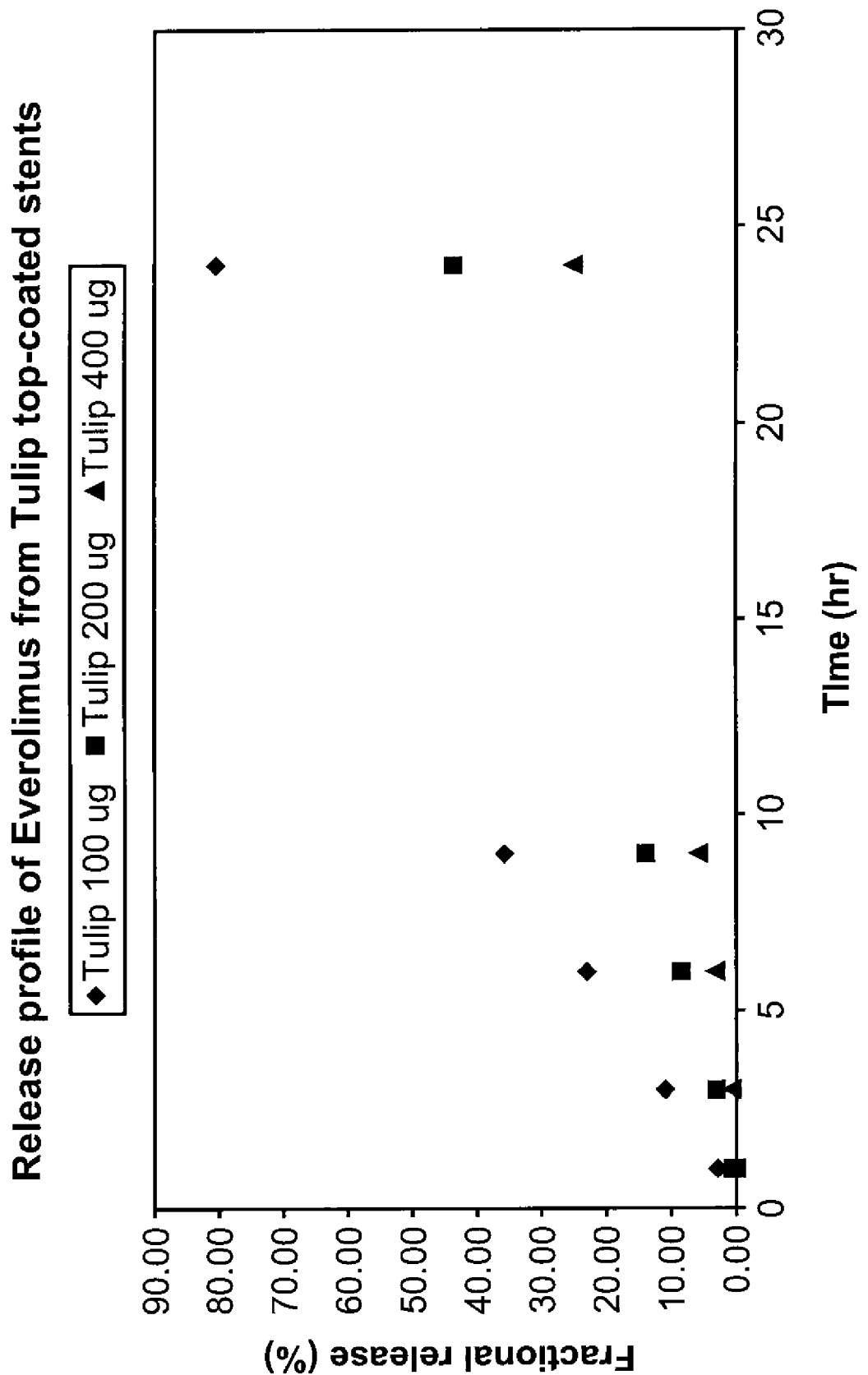
FIG. 2 shows the drug-release data of the stents as described in Example 1 in PBS-Triton system.

The stents coated according to the above configurations are shown in FIGS. 1a, 1b and 1c, which show the good mechanical integrity of these coatings. The stents were subjected to an in vitro drug release study. FIG. 2 shows the release profile of these coatings in a PBS-Triton buffer system. The data from porcine serum are listed in Table 1. The results showed that the coating of configuration 1 released about 25% of the drug on day one and 75% on day two. A linear release profile was observed for all the coatings. It is noteworthy that the release rate decreases in a linear relationship to the amount of PEAs used in the coatings (Configuration 1: 100 μg PEA, Configuration 2: 200 μg PEA, and Configuration 3: 400 μg PEA), clearly showing membrane controlled drug release characteristics.

TABLE 1

Drug release rate in porcine serum after 24 and 72 hours

| | Sample | | | | | |
|---|---|---|---|---|---|---|
| | Configuration 1 | | Configuration 2 | | Configuration 3 | |
| Time | 24 hr | 72 hr | 24 hr | 72 hr | 24 hr | 72 hr |
| Release % | 25.9% | 73% | 12.4% | NA | 8.4% | NA |

Example 2

Stents Coated with PEA-TEMPO

A first composition is prepared by mixing the following components:
(a) about 2.0% (w/w) of the polymer PEA-TEMPO
(b) the balance, ethyl alcohol The first composition can be applied onto the surface of bare 12 mm small VISION™ stent (Guidant Corp.). The coating can be sprayed and dried to form a primer layer. A spray coater can be used having a 0.014 round nozzle maintained at ambient temperature with a feed pressure 2.5 psi (0.17 atm) and an atomization pressure of about 15 psi (1.02 atm). About 20 μg of the coating can be applied per one spray pass. Between spray passes, the stent can be dried for about 10 seconds in a flowing air stream at about 50° C. About 110 μg of wet coating can be applied. The stents can be baked at about 50° C. for about one hour, yielding a primer layer composed of approximately 100 µg of PEA-TEMPO.

Example 3

Stents Coated with PEA-TEMPO and Poly(imino carbonate)

A second composition can be prepared by mixing the following components:
(a) about 1.8% (w/w) of the polymer of PEA-TEMPO;
(b) about 0.2% (w/w) of poly(imino carbonate)
(b) about 0.5% (w/w) of everolimus; and
(c) the balance, a solvent mixture of ethyl alcohol and dimethylformamide (80/20) (w/w)

The second composition can be applied onto the dried primer layer to form the drug-polymer layer, using the same spraying technique and equipment used for applying the primer layer. About 300 µg of wet coating can be applied followed by drying and baking at about 60° C. for about 2 hours, yielding a dry drug-polymer layer having solids content of about 275 µg.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. An implantable device comprising a coating, the coating comprising:
   a poly(ester amide) (PEA) polymer comprising a polymer chain having amide groups in the chain, and
   a material for hydrogen-bonding with the PEA,
   wherein the polymer chain of one molecule of the PEA polymer hydrogen-bonds to a molecule of the material for hydrogen-bonding, which in turn hydrogen-bonds to the polymer chain of another molecule of the PEA polymer.

2. The implantable device of claim 1, wherein the PEA polymer comprises diacid, diol, and amino acid subunits in its backbone.

3. The implantable device of claim 1, wherein the PEA polymer is co-poly-{[N,N'-sebacoyl-bis-(L-leucine)-1,6-hexylene diester]-[N,N'-sebacoyl-L-lysine benzyl ester]} (PEA-Bz) or co-poly{[N,N'-sebacoyl-bis-(L-leucine)-1,6-hexylene diester]-[N,N'-sebacoyl-L-lysine 4-amino-TEMPO amide]}(PEA-TEMPO).

4. The implantable device of claim 3, further comprising a biobeneficial material selected from garlic oil, fullerene, heparin, hirudin, fibrin, hyaluronic acid, hydrophobically modified hyaluronic acid, chondroitan sulfate, glycosaminoglycans, chitin, poly(styrene sulfonate), or combinations thereof.

5. The implantable device of claim 1, wherein the material for hydrogen-bonding with PEA is selected from the group consisting of non-degradable polymers, biodegradable polymers and combinations thereof,
   wherein the non-degradable polymer has a molecular weight below about 40,000 Daltons, and
   wherein the biodegradable polymer can degrade into fragments having a molecular weight below about 40,000 Daltons.

6. The implantable device of claim 1, wherein the material for hydrogen-bonding with PEA is selected from the group consisting of polymers or copolymers of monomers containing a hydroxyl group, a carboxyl group, an ether group, a carbonyl group, a urethane group, a urea group, or an amino group, poly(vinyl alcohol), poly(vinyl alcohol-co-vinyl acetate), polyacrylic acid, polymethacrylic acid, poly(acrylamide), poly(hydroxypropyl methacrylamide), poly(2-hydroxyethyl methacrylate), poly(2-methoxyethyl methacrylate), poly(2-ethoxyethyl methacrylate), poly(2-methoxyethyl acrylate), poly(vinyl pyrrolidone), poly (pyrrole), poly(ethylene-co-vinyl alcohol), non-water soluble cellulose acetate, non-water soluble hydroxyethyl cellulose, non-water soluble hydroxypropyl cellulose, cellulose ethers, methyl cellulose and ethyl cellulose, poly(urethanes), poly (urethane-ureas), poly(ureas), poly(tetramethylene glycol), poly(propylene glycol), poly(ethylene glycol), poly(imino carbonates), peptides, gelatin, collagen, non-water soluble chitosan, agarose, elastin, poly(alginic acid), alginate, dextrose, dextran, poly(glutamic acid), poly(lysine), copolymers containing poly(ethylene glycol) and polybutylene terephthalate segments, poly(aspartic acid), poly(leucine), poly(leucine-co-hydroxyethyl glutamine), poly(benzyl glutamate), poly(glutamic acid-co-ethyl glutamate), poly(amino acids), poly(ortho esters), poly(anhydrides), poly(D,L-lactic acid), poly (L-lactic acid), poly(glycolic acid), copolymers of poly (lactic) and glycolic acid, poly(phospho esters), poly(-hydroxybutyrate), poly(caprolactone), poly(trimethylene carbonate), poly(oxaesters), poly(oxaamides), poly(ethylene carbonate), poly(propylene carbonate), poly(phosphoesters), poly(phosphazenes), copolymers thereof with poly(ethylene glycol), and combinations thereof.

7. The implantable device of claim 1, wherein the material for hydrogen-bonding with PEA is a-copolymer containing poly(ethylene glycol) and polybutylene terephthalate segments.

8. The implantable device of claim 7, wherein the PEA and the copolymer containing poly(ethylene glycol) and polybutylene terephthalate segments form a blend.

9. The implantable device of claim 7, wherein the PEA forms a PEA layer of coating, and wherein the copolymer containing poly(ethylene glycol) and polybutylene terephthalate segments forms a layer of coating separate from the PEA layer of coating.

10. The implantable device of claim 1, further comprising a biobeneficial material selected from garlic oil, fullerene, heparin, hirudin, fibrin, hyaluronic acid, hydrophobically modified hyaluronic acid, chondroitan sulfate, glycosaminoglycans, chitin, poly(styrene sulfonate), or combinations thereof.

11. The implantable device of claim 1, further comprising a biobeneficial material garlic oil, fullerene, heparin, hirudin, fibrin, hyaluronic acid, hydrophobically modified hyaluronic acid, chondroitan sulfate, glycosaminoglycans, chitin, poly (styrene sulfonate), or combinations thereof.

12. The implantable device of claim 1, wherein the material for hydrogen bonding with PEA is selected from the group consisting of dendrimers, star-shaped molecules, absorbable glass, and combinations thereof,
   wherein the dendrimer or star-shaped molecule has a group selected from the group consisting of —$NH_2$, —COOH, —OH groups and combinations thereof, and
   wherein the absorbable glass comprises Fe, Ca, or phosphate, or combinations thereof.

13. The implantable device of claim 1, wherein the material for hydrogen bonding with PEA is a bioactive component selected from the group consisting of laminin V, silk elastin, hyaluronic acid-benzyl ester, resten NG, antisense oligonucleotide fragment with antiproliferative properties, MMPI, cellulose acetate-co-pentasaccharide, and combinations thereof.

14. The implantable device of claim 1, wherein the implantable device is a stent.

15. The implantable device of claim 14, wherein the coating further comprises a therapeutic agent.

16. The implantable device of claim 15, wherein the therapeutic agent is selected from the group consisting of paclitaxel, docetaxel, estradiol, nitric oxide donors, super oxide dismutases, super oxide dismutases mimics, 4-amino-2,2,6,6-tetramethylpiperidine-1-oxyl(4-amino-TEMPO), tacrolimus, dexamethasone, rapamycin, rapamycin derivatives, 40-O-(2-hydroxy)ethyl-rapamycin (everolimus), 40-O-(3-hydroxy)propyl-rapamycin, 40-O-[2-(2-hydroxy)ethoxy]ethyl-rapamycin, and 40-O-tetrazole-rapamycin, ABT-578, clobetasol, progenitor cell capturing antibody, prohealing drugs, prodrugs thereof, co-drugs thereof, and a combination thereof.

\* \* \* \* \*